United States Patent [19]

Vierbicky

[11] 4,125,024
[45] Nov. 14, 1978

[54] MOLTEN METAL SAMPLING DEVICE

[75] Inventor: Van L. Vierbicky, Weirton, W. Va.

[73] Assignee: National Steel Corporation, Pittsburgh, Pa.

[21] Appl. No.: 794,241

[22] Filed: May 5, 1977

[51] Int. Cl.$^2$ ............................................. G01N 1/12
[52] U.S. Cl. ............................................. 73/425.4 R
[58] Field of Search ..................... 73/425.4 R, DIG. 9

[56] References Cited

U.S. PATENT DOCUMENTS 4,046,016   9/1977   Hackett ............................. 73/425.4

Primary Examiner—S. Clement Swisher
Attorney, Agent, or Firm—Shanley, O'Neil & Baker

[57] ABSTRACT

A device for sampling heats of molten metal includes a mold cavity which has an inlet which may be in the form of a tube projecting outwardly therefrom with the open end of the tube being closed and sealed prior to the sampling step by a metallic cap which will melt in the molten metal heat. The sealed end of the tube is enclosed within a diffusion chamber having an inlet closed with a cap which will be melted or vaporized by the metal heat and which normally retains a quantity of a suitable oxygen-fixing agent such as aluminum or titanium, for example, within the chamber. Molten metal entering the diffusion chamber immediately melts the fixing agent which is quickly dissolved by and thoroughly diffused through the molten metal in the chamber before the metal cap on the end of the tube melts to permit the molten metal with the oxygen-fixing agent diffused therethrough to flow into the sample-forming mold cavity.

45 Claims, 4 Drawing Figures

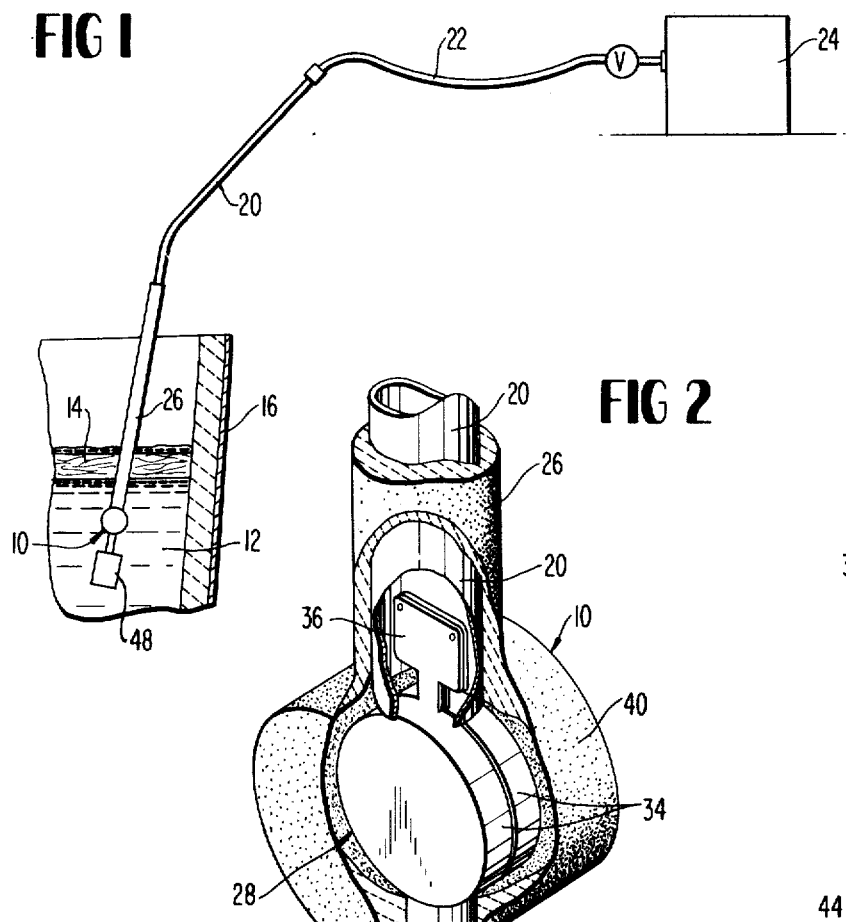
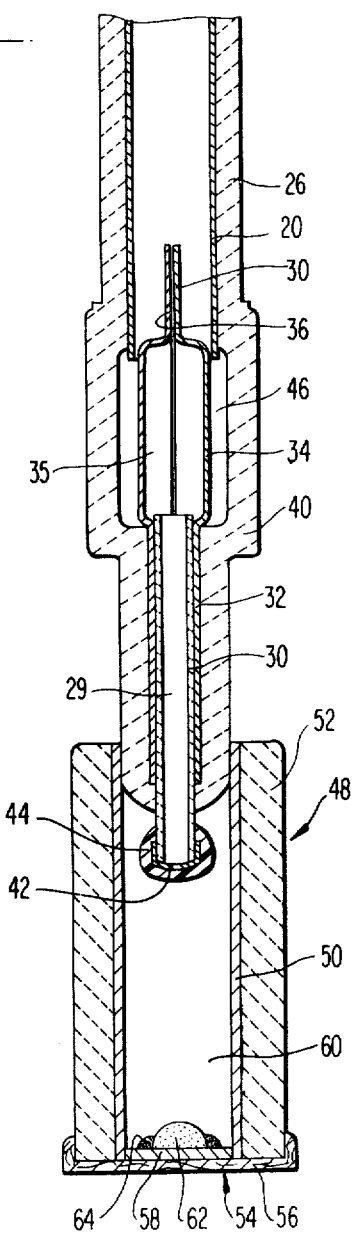
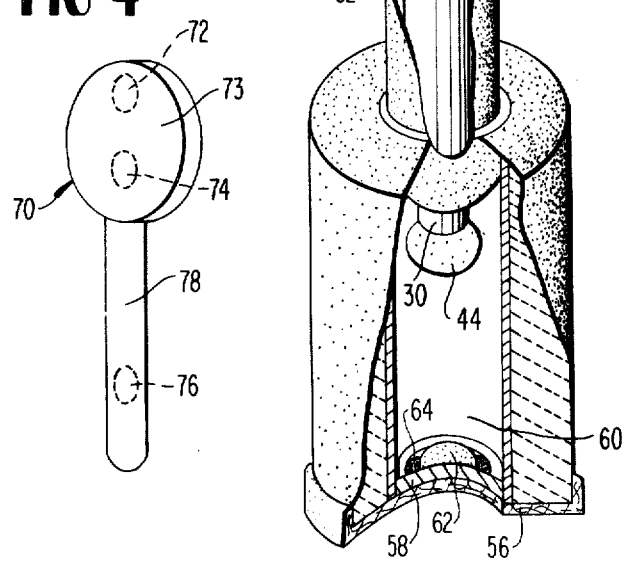
FIG 1
FIG 2
FIG 3
FIG 4

MOLTEN METAL SAMPLING DEVICE

BACKGROUND OF THE INVENTION

1. Field of the Invention

This invention relates to means for obtaining a sample of molten metal from a heat of the molten metal, and more particularly to a novel apparatus for obtaining a solidified sample of metal from a heat of the molten metal.

2. Description of the Prior Art

In the production and refinement of metals, the numerous variables encountered make it necessary to obtain samples of the metal for constituent analysis at various stages during the refining process. For example, in the production of steel in a basic oxygen furnace, in order to assure the desired composition of the final product, it is necessary to obtain one or more solidified samples from the molten metal in the furnace, and the ladle after tap, immediately analyze the sample and utilize the results of this analysis for determining further processing such as the length of time of any further blowing required, or amount of deoxidant required to "kill" the steel in the ladle or further in the process. One important element of the analysis is the amount of oxygen in the melt at the time of taking the sample and, to obtain this information, the sample is normally "killed" by a small quantity of an oxygen-fixing agent such as aluminum or titanium which is placed in the sample mold cavity and melted by the liquid steel which forms the sample. The oxygen in the sample then combines with the fixing agent to form stable compounds which are retained in the sample and may be detected and measured during the subsequent analysis.

Numerous devices have been developed in the past for obtaining solidified samples from a melt of steel, which samples are frequently in the form of elongated cylindrical pins or relatively flat cylindrical discs. Sampling devices and procedures have been developed for simultaneously obtaining both a pin-type and a disc-type sample, one such apparatus being disclosed in U.S. Pat. No. 3,915,014 assigned to the assignee of this invention. In such an apparatus, the test sample, generally referred to as a lollipop sample, is obtained by immersing the end of a mold structure into a heat of the metal. The molten metal flows either by ferrostatic pressure alone or in combination with the application of suction into the lollipop-shaped mold cavity, with the handle of the lollipop forming the pin sample and the body of the lollipop forming the disc sample. Other examples of prior art sampling devices include U.S. Pat. No. 3,656,350 which employs a pair of metal cup-shaped elements defining a tortuous path for the molten steel and the oxygen-fixing agent to follow before entering the sample mold cavity, and U.S. Pat. No. 3,704,621 which discloses a dipper-type sampling device having a sample chamber containing a quantity of an oxygen-fixing agent and closed by a closure which is destroyed by the heat of the steel.

While the known prior art sampling devices have met with varying degrees of approval and success, the ever-increasing demands on the steel industry for strict product quality control places even greater emphasis on the necessity for obtaining reliable test samples. One difficulty which has been encountered with the prior art sampling devices is the fact that the oxygen-fixing agent normally placed within the mold chamber (or in the case of, for example, U.S. Pat. No. 3,656,350, in one of the metal cups to which the molten steel must flow in its path into the sample mold cavity) has not been uniformly dispersed through the metal of the sample. As a result, the steel sample was not always thoroughly killed so that an accurate oxygen content was not always reflected upon analysis of the sample.

Another difficulty encountered in obtaining suitable samples in the past has been the entry of impurities into the sample mold from the layer of slag or casting powder normally covering the heat of molten steel.

It is therefore a primary object of the present invention to provide an improved molten metal sampling apparatus which will enable a more accurate and reliable analysis of the metal sample.

SUMMARY OF THE INVENTION

In the attainment of the foregoing and other objects and advantages of the present invention, an important feature resides in the provision of a separate, sealed diffusion chamber into which the molten steel enters and in which it is retained for a brief interval before entering the sample mold cavity. The diffusion chamber is somewhat larger than the sample mold cavity and contains a quantity of an oxygen-fixing agent which is quickly melted and dissolved by the molten steel within the chamber. The solution of steel and oxygen-fixing agent is retained in the diffusion chamber for a sufficient time for the fixing agent to be diffused throughout the steel in the chamber before the metal melts a cap closing the entry end of the mold cavity. The interior of the sample device may be connected to a source of vacuum, if necessary or desirable, to assist the ferrostatic head of the molten steel in filling the sample mold cavity.

BRIEF DESCRIPTION OF THE DRAWING

Other objects and advantages of the invention will become apparent from the detailed description contained hereinbelow, taken in conjunction with the drawings, in which:

FIG. 1 is a schematic view illustrating a preferred embodiment of the invention in its environment of use;

FIG. 2 is a perspective view of a preferred embodiment of the invention, with parts broken away to more clearly illustrate other parts;

FIG. 3 is a vertical sectional view of the apparatus shown in FIG. 2; and

FIG. 4 is a perspective view of a lollipop sample taken with the sampler of the present invention.

DESCRIPTION OF THE PREFERRED EMBODIMENT

Referring now to the drawings in detail, a sampling apparatus according to the present invention, indicated generally by the reference numeral 10, is illustrated as having its lower, sample-receiving end submerged in a bath, or pool of molten steel 12 having a layer of slag or casting powder 14 floating thereon and retained in a refractory-lined vessel 16. The sampling device 10 is supported on the lower end of a long rigid conduit or pipe 20, the upper end of which may be open to the atmosphere or, if desired, attached through a flexible hose 22 to a suitable vacuum source indicated generally at 24. The portion of the pipe 20 subjected to the extreme temperature of the molten steel is protected by a refractory sheath 26.

Referring to FIG. 2, the sampling mold components of the device, indicated generally at 28, and the thermal insulating refractory housing therefor, indicated generally by the reference numeral 40, may be generally similar to the structure shown in U.S. Pat. No. 3,915,014, reference to which may be had for a more detailed description of this structure. As illustrated, the mold cavity includes a pin sample portion 29 defined by an elongated fused quartz conduit or tube 30 supported by opposed complementary half-tubular portions 32 of a pair of metal members each of which terminate in shallow pan-like sections 34 arranged in opposed relation to define a cylindrical disc portion 35 of the mold cavity within the interior of housing 40 at the inner end of the quartz tube.

A pair of metallic ears 36 formed one on each of the metallic mold sections 34 and projecting upwardly therefrom cooperate to join the two mold sections together in slightly spaced relation to provide gaseous communication between the interior of the mold cavity 35 and the interior of pipe 20. Preferably, the ears 36 are spot-welded together and are shaped to be wedged into and frictionally support the structure on the end of the pipe 20 during molding of the impervious refractory housing assembly 40 which completely encases the metallic mold elements and the bottom end of pipe 20, and which has its bottom wall sealed in fluid-tight relation to the lower end of the quartz tube 30 with the outer end of tube 30 extending therethrough, and its upper end connected to the end of the support pipe 20. Preferably, the refractory sheath 26 is formed as an integral part of housing 40 though, if desired, these components may be separately formed and subsequently joined with a suitable refractory or other heat-resistant material to provide a gas-tight juncture.

As seen in FIG. 3, the outer or lower end of the fused quartz tube 30 is closed by a closure in the form of a crimped metal cap 42. Preferably, a suitable plastic coating 44 is also applied to the lower end of the tube 30, with the plastic coat covering cap 42 and forming a fluid-tight seal with tube 30. Also as shown in FIG. 3, the disc sample mold cavity defined by the pan-shaped metal segments 34 is preferably located within a hollow chamber 46 which, together with the lower open end portion of pipe 20 defines an interior cavity that provides fluid communication between the pipe 20 and the mold cavity to assure venting of the mold cavity as it is filled with the molten steel.

Mounted upon and projecting from the outer or bottom end of refractory housing 40 is a downwardly-open sample diffusion chamber assembly 48. As illustrated, the assembly 48 consists of an elongated metal sleeve 50 having one open end telescopingly received on and in sealing relation with the bottom end of housing 40 and its other end extending downwardly below the bottom end of the fused quartz tube 30. An insulating refractory housing 52 is molded on and provides thermal insulation for the outer surface of sleeve 50. It is understood that the diffusion chamber may be of any desired shape, such as cylindrical, frusto-conical, or the like and that, if desired, the metal sleeve 50 may be eliminated. Further, the chamber may be integrally molded with the housing 40 if desired.

The inlet at the bottom end of assembly 48 is sealed by a closure 54 which is destructible by the heat of the metal to be sampled. The closure 54 includes an outer cap member 56 preferably formed from a dense paper or other suitable material which will be vaporized or burned away as the device penetrates the layer of slag 14 and enters the molten metal bath 12. This vaporization of the cap 56 prevents the slag from adhering to or being trapped beneath the end of the device, thereby essentially precluding slag from entering the diffusion chamber 60 upon destruction of the closure 54.

The closure 54 also includes an inner member in the form of a metal disc 58 fitted snugly within the bottom open end of sleeve 50. This disc 50 has a thickness and a melting temperature to be destroyed by the heat of the molten metal only after a sufficient time to permit penetration of the sampling device to the desired depth. Thus, although the diffusion chamber 60 is filled from the bottom, the closure 54 both effectively excludes from the chamber slag or other foreign material floating on the top of the molten metal and prevents filling of the chamber until it has penetrated to the depth required to obtain a representative sample.

A suitable quantity of an oxygen-fixing agent 62 is retained on the inner surface of disc member 58, as by a bead of adhesive material 64. The oxygen-fixing agents 62 may be any suitable material conventionally used for this purpose, and is retained in the lower portion of the diffusion chamber 60 so that, as the closure 54 is destroyed by the heat of the molten steel, it will be immediately contacted and melted by molten steel rushing into the chamber under the ferrostatic pressure of the liquid steel 12. It is also contemplated that, in some applications, the metal disc 58 may be made of or contain the oxygen-fixing agent.

The oxygen-fixing agents such as germanium or aluminum in the liquid state, are soluble in the molten steel and, as they are melted, very quickly diffuse throughout the volume of steel in the chamber 60. It is, therefore, only necessary to retain the steel in the diffusion chamber for a relatively short time, which time may readily be controlled by the selection of material and the thickness of the metal cap 42 and/or the plastic sealing material 44. In practice, it has been found that a cap 42 formed of a mild, low carbon steel having a thickness of 0.005 inches will provide sufficient time delay between the steel entering the diffusion chamber and the molten steel-oxygen-fixing agent solution entering the sample mold cavity to assure diffusion of the oxygen-fixing agent throughout the material forming the sample.

As illustrated in FIGS. 2 and 3, the volume of the mixing chamber 60 is somewhat greater than the volume of the lollipop-shaped sample mold cavity and preferably at least about 1 ¼ times the volume of the sample mold cavity. The reason for this excess volume of the diffusion chamber is to assure that all metal entering the sample mold cavity will have the oxygen-fixing agent diffused therethrough, or stated differently, to assure that "unkilled" steel from the molten steel bath 12 does not enter the sample mold cavity. Further, the bottom end of the quartz tube 30 preferably terminates at a point at least slightly below the top of the diffusion chamber 60 so that any slag or other impurities which may enter the diffusion chamber will tend to rise above the top of the entry end of the quartz tube 30, thereby further assuring that impurities will be eliminated from the sample. However, the molten metal in this small portion of the volume of the diffusion chamber above the end of the quartz tube 30 will not enter the sample, thereby requiring the volume of the chamber 60 between the end of tube 30 and the open inlet to the chamber to be at least as great as and preferably slightly greater than the volume of the sample mold cavity when the tube 30 projects into the diffusion chamber as described.

Since the diffusion chamber 60 has its lower end sealed with a destructable closure member 54 which tends to eliminate slag or other impurities from the chamber, the plastic sealing material 44 over the metal cap 42 may not be required. However, the plastic sealing material 44 encompassing the metal cap 42 may be utilized to provide further insurance that slag or other impurities do not enter the mold cavity.

The sampling apparatus described thus far is equally well adapted for use with and without the vacuum apparatus 24. When vacuum is not applied, the top end of the pipe 20 is open to atmosphere, and ferrostatic pressure in the vessel 16 will cause the molten metal to flow into the device. Thus, the metal will fill the diffusion chamber 16 upon destruction of the bottom closure 54, to a level above the lower end of tube 30 and thereafter be forced into the sample mold cavity upon destruction of the cap 42.

A number of sampling devices constructed essentially as illustrated in the drawings herein were employed to take samples from a number of melts of steel in a ladle tapped from a basic oxygen furnace, and the results of the analysis of these samples were compared with samples taken contemporaneously therewith by use of a dipper-type sampling device having two sample chambers. The samples were analyzed for the content of carbon, manganese, sulfur, phosphorus, silicon, tin, copper, chromium, nickel, molybdenum, aluminum, nitrogen and oxygen. With the exception of the percentage of oxygen, the analyis of the samples taken by the dipper-type (p-12) sampler and the sampler according to this invention (V) were comparable. However, the amount of oxygen in the samples taken by the two devices varied widely, with the amount in the samples taken by the sampler according to the present invention corresponding much more closely to the amount contained in the steel actually poured (Final) from the BOF. The results of these tests are as follows:

| Heat # | P-12 | Oxygen Content (parts per million) P-12 | V | Final |
| --- | --- | --- | --- | --- |
| 80593 | 307 | 267 | 81 | 71 |
| 80814 | 266 | 355 | 101 | 66 |
| 81243 | 261 | Bad Test | 106 | 78 |
| 81432 | 158 | 161 | 105 | 89 |
| 11275 | 135 | 143 | 88 | 52 |
| 11301 | 162 | 152 | 112 | 82 |
| 11326 | 235 | 157 | 111 | 57 |
| 11349 | 144 | 169 | 108 | 66 |

The results of the tests outlined above clearly indicate that the samples taken with the sampler according to the present invention more accurately represent the actual oxygen content of the steel in the ladle receiving steel from the BOF than do the samples taken with the commercially available and widely-used dipper-type sampler. From this, it is believed apparent that a more accurate control of the processing can be obtained by use of this invention.

Another advantage of the present invention is that the uniform diffusion of the oxygen-fixing agent through the sample enables the use of a smaller amount of this material. To demonstrate the efficiency of the diffusion chamber, a lollipop sample 70 shown in FIG. 4 was checked to determine the distribution of the oxygen-fixing agent through the sample. The sample tested was killed with germanium and three borings were made in the sample to determine the distribution of the germanium. The tests revealed the first boring taken from the top portion of the disc sample 73, in the area designated 72 in FIG. 4, contained 0.292 percent germanium while the material taken from the boring 74 at the bottom portion of the disc contained 0.289 percent germanium. The boring on the area designated 76, near the bottom of the pin 78, contained 0.211 percent germanium. An average of these three readings indicate that 44% of the germanium used in the diffusion chamber was contained within the sample, and the amount of germanium in the lowest area tested was greatly in excess of that required for complete killing of the steel. The sampler used to take the samples tested had a diffusion chamber volume approximately 1 ½ times the volume of the sample mold chamber.

All of the tests discussed above were taken with a sampler according to the present invention without the use of vacuum applied to the pipe 20.

It is understood that various modifications and changes in the structure described may be made without departing from the invention. For example, while the invention is described in relation to the formation of a lollipop sample, it may readily be adapted to the formation of other sample configurations such as disc samples or pin samples. Thus, to form a pin sample, the mold cavity portion 29 defined by the interior bore of the quartz tube 30 defines the entire mold cavity, and the inner end of the tube is placed in direct fluid communication with the interior of pipe 20 within the interior of housing 40 to permit venting. Similarly, when a disc or other shaped sample is desired, an opening from the diffusion chamber and normally closed by the heat-destructible cap or other shaped closure member may lead directly to the mold cavity. Accordingly, while I have disclosed and described a preferred embodiment of my invention, I wish it understood that I do not intend to be restricted solely thereto, but rather that I do intend to include all embodiments thereof which would be apparent to one skilled in the art and which come within the spirit and scope of my invention.

I claim:

1. A molten metal sampling device including an insulating housing having a mold cavity therein for forming a solidified sample of the metal, said sampling device comprising a diffusion chamber having an inlet therein for receiving molten metal, means defining an opening between said mold cavity and said diffusion chamber, first closure means closing said opening, said first closure means being destructible by the heat of the molten metal to be sampled to thereby provide communication between said diffusion chamber and said mold cavity only after molten metal is received in said diffusion chamber, and second closure means closing said inlet, said second closure means being destructible by the heat of molten metal to thereby admit molten metal into said diffusion chamber when the sampling device is submerged in the molten metal to be sampled.

2. The invention as defined in claim 1 wherein said first closure means comprises a closure member having a thickness and a melting temperature such that it will be destroyed by the heat of molten metal entering the diffusion chamber only after a predetermined time to thereby retain the molten metal in the diffusion chamber for said predetermined time before communication is established between said diffusion chamber and said mold cavity.

3. The invention as defined in claim 2 further comprising an elongated tubular member having a bore extending therethrough defining said opening between said mold cavity and said diffusion chamber, said tubular member extending through and being sealed in one wall of the insulating housing and having an outer end projecting outwardly from said one wall into said diffusion chamber, said first closure means being mounted on and closing said outer end of said tubular member.

4. The invention as defined in claim 3 wherein said first closure member comprises a metal cap mounted on and closing the outer end of said tubular member.

5. The invention as defined in claim 4 wherein said first closure means further comprises a layer of plastic material covering said metal cap and sealing said metal cap on the end of said tubular member.

6. The invention as defined in claim 5 wherein the portion of said diffusion chamber between said outer end of said tubular member and the inlet has a volume at least as great as the volume of the mold cavity in the sampling device.

7. The invention as defined in claim 6 wherein said diffusion chamber has a volume at least about 1.5 times the volume of the mold cavity.

8. The invention as defined in claim 7 wherein the bore of said tubular member defines at least a portion of said mold cavity.

9. The invention as defined in claim 8 wherein said second closure means comprises an outer layer of nonmetallic material and an inner layer of metal.

10. The invention as defined in claim 9 further comprising an oxygen-fixing agent which is soluble in the metal to be sampled retained in said diffusion chamber in position to be contacted by the molten metal entering the diffusion chamber, and wherein said predetermined time delay is sufficient to permit diffusion of said oxygen-fixing agent substantially throughout the liquid metal in the diffusion chamber before it enters the mold cavity.

11. The invention as defined in claim 10 wherein said oxygen-fixing agent is a metal, and wherein said inner layer of said second closure is formed of or contains said oxygen-fixing agent.

12. The invention as defined in claim 11 wherein said diffusion chamber comprises an elongated cylindrical member having one end rigidly supported on and sealed to said one wall of the sampling device and having its other end projecting outwardly therefrom past the outer end of said tubular member, said second closure means being mounted on and sealingly closing said other end of said cylindrical member.

13. The invention as defined in claim 3, wherein said diffusion chamber has a volume at least about 1.5 times the volume of the mold cavity.

14. The invention as defined in claim 13, further comprising an oxygen-fixing agent which is soluble in the metal to be sampled retained in said diffusion chamber in position to be contacted by the molten metal entering the diffusion chamber, and wherein said predetermined time delay is sufficient to permit diffusion of said oxygen-fixing agent substantially throughout the liquid metal in the diffusion chamber before it enters the mold cavity.

15. The invention as defined in claim 3, wherein the bore of said tubular member defines at least a portion of said mold cavity.

16. The invention as defined in claim 3, further comprising an oxygen-fixing agent which is soluble in the metal to be sampled retained in said diffusion chamber in position to be contacted by the molten metal entering the diffusion chamber, and wherein said predetermined time delay is sufficient to permit diffusion of said oxygen-fixing agent substantially throughout the liquid metal in the diffusion chamber before it enters the mold cavity.

17. The invention as defined in claim 2, wherein said diffusion chamber has a volume at least about 1.5 times the volume of the mold cavity.

18. The invention as defined in claim 13, wherein said second closure means comprises an outer layer of nonmetallic material and an inner layer of metal.

19. The invention as defined in claim 13, further comprising an oxygen-fixing agent which is soluble in the metal to be sampled retained in said diffusion chamber in position to be contacted by the molten metal entering the diffusion chamber, and wherein said predetermined time delay is sufficient to permit diffusion of said oxygen-fixing agent substantially throughout the liquid metal in the diffusion chamber before it enters the mold cavity.

20. The invention as defined in claim 2, wherein said second closure means comprises an outer layer of nonmetallic material and an inner layer of metal.

21. The invention as defined in claim 20, further comprising an oxygen-fixing agent which is soluble in the metal to be sampled retained in said diffusion chamber in position to be contacted by the molten metal entering the diffusion chamber, and wherein said predetermined time delay is sufficient to permit diffusion of said oxygen-fixing agent substantially throughout the liquid metal in the diffusion chamber before it enters the mold cavity.

22. The invention as defined in claim 21, wherein said oxygen-fixing agent is a metal, and wherein said inner layer of said second closure is formed of or contains said oxygen-fixing agent.

23. The invention as defined in claim 2, wherein said diffusion chamber comprises an elongated cylindrical member having one end rigidly supported on and sealed to said one wall of the sampling device and having its other end projecting outwardly therefrom past the outer end of said tubular member, said second closure means being mounted on and sealingly closing said other end of said cylindrical member.

24. The invention as defined in claim 2, further comprising an oxygen-fixing agent which is soluble in the metal to be sampled retained in said diffusion chamber in position to be contacted by the molten metal entering the diffusion chamber, and wherein said predetermined time delay is sufficient to permit diffusion of said oxygen-fixing agent substantially throughout the liquid metal in the diffusion chamber before it enters the mold cavity.

25. The invention as defined in claim 1, further comprising an elongated tubular member having a bore extending therethrough defining said opening between said mold cavity and said diffusion chamber, said tubular member extending through and being sealed in one wall of the insulating housing and having an outer end projecting outwardly from said one wall into said diffusion chamber, said first closure means being mounted on and closing said outer end of said tubular member.

26. The invention as defined in claim 25, wherein said first closure member comprises a metal cap mounted on and closing the outer end of said tubular member.

27. The invention as defined in claim 26 wherein said first closure means further comprises a layer of plastic material covering said metal cap and sealing said metal cap on the end of said tubular member.

28. The invention as defined in claim 21, wherein said diffusion chamber has a volume at least about 1.5 times the volume of the mold cavity.

29. The invention as defined in claim 21, wherein the bore of said tubular member defines at least a portion of said mold cavity.

30. The invention as defined in claim 21, wherein said second closure means comprises an outer layer of non-metallic material and an inner layer of metal.

31. The invention as defined in claim 25, wherein the portion of said diffusion chamber between said outer end of said tubular member and the inlet has a volume at least as great as the volume of the mold cavity in the sampling device.

32. The invention as defined in claim 25, wherein said diffusion chamber has a volume at least about 1.5 times the volume of the mold cavity.

33. The invention as defined in claim 25, wherein the bore of said tubular member defines at least a portion of said mold cavity.

34. The invention as defined in claim 25, wherein said second closure means comprises an outer layer of non-metallic material and an inner layer of metal.

35. The invention as defined in claim 25, further comprising an oxygen-fixing agent which is soluble in the metal to be sampled retained in said diffusion chamber in position to be contacted by the molten metal entering the diffusion chamber.

36. The invention as defined in claim 1, wherein said diffusion chamber has a volume at least about 1.5 times the volume of the mold cavity.

37. The invention as defined in claim 36, wherein said second closure means comprises an outer layer of non-metallic material and an inner layer of metal.

38. The invention as defined in claim 32, wherein said diffusion chamber comprises an elongated cylindrical member having one end rigidly supported on and sealed to said one wall of the sampling device and having its other end projecting outwardly therefrom past the outer end of said tubular member, said second closure means being mounted on and sealingly closing said other end of said cylindrical member.

39. The invention as defined in claim 36, further comprising an oxygen-fixing agent which is soluble in the metal to be sampled retained in said diffusion chamber in position to be contacted by the molten metal entering the diffusion chamber.

40. The invention as defined in claim 36, wherein said diffusion chamber comprises an elongated cylindrical member having one end rigidly supported on and sealed to said one wall of the sampling device and having its other end projecting outwardly therefrom past the outer end of said tubular member, said second closure means being mounted on and sealingly closing said other end of said cylindrical member.

41. The invention as defined in claim 1, wherein said second closure means comprises an outer layer of non-metallic material and an inner layer of metal.

42. The invention as defined in claim 41, further comprising an oxygen-fixing agent which is soluble in the metal to be sampled retained in said diffusion chamber in position to be contacted by the molten metal entering the diffusion chamber.

43. The invention as defined in claim 42, wherein said oxygen-fixing agent is a metal, and wherein said inner layer of said second closure is formed of or contains said oxygen-fixing agent.

44. The invention as defined in claim 41 wherein said diffusion chamber comprises an elongated cylindrical member having one end rigidly supported on and sealed to said one wall of the sampling device and having its other end projecting outwardly therefrom past the outer end of said tubular member, said second closure means being mounted on and sealingly closing said other end of said cylindrical member.

45. The invention as defined in claim 1, wherein said diffusion chamber comprises an elongated cylindrical member having one end rigidly supported on and sealed to said one wall of the sampling device and having its other end projecting outwardly therefrom past the outer end of said tubular member, said second closure means being mounted on and sealingly closing said other end of said-cylindrical member.

* * * * *